United States Patent [19]

Basseres et al.

[11] Patent Number: 5,618,725
[45] Date of Patent: Apr. 8, 1997

[54] OLEOPHILIC BIODEGRADING ADDITIVE AND METHOD OF TREATING HYBROCARBON POLLUTED MEDIUM

[75] Inventors: Anne Basseres, Pau; Patrick Eyraud, Poey De Lescar; Alain Ladousse, Pau, all of France

[73] Assignee: Elf Aquitaine, Courbeuoie, France

[21] Appl. No.: 387,723

[22] PCT Filed: Aug. 27, 1993

[86] PCT No.: PCT/FR93/00834

§ 371 Date: May 8, 1995

§ 102(e) Date: May 8, 1995

[87] PCT Pub. No.: WO94/05773

PCT Pub. Date: Mar. 17, 1994

[30] Foreign Application Priority Data

Aug. 31, 1992 [FR] France .................. 92 10409

[51] Int. Cl.$^6$ .................. C07C 209/02
[52] U.S. Cl. .................. 435/262; 71/11; 71/15; 562/514; 562/553; 530/402; 530/841; 530/857; 426/574; 426/641; 426/643; 426/646; 426/656; 426/657
[58] Field of Search .................. 435/262; 71/11, 71/15; 562/514, 553; 530/402, 841, 857; 426/574, 641, 643, 646, 656, 657

[56] References Cited

U.S. PATENT DOCUMENTS

| 3,880,824 | 4/1975 | Rao et al. .................. 426/656 |
|---|---|---|
| 3,952,115 | 4/1976 | Damico et al. .................. 426/641 |
| 4,925,802 | 5/1990 | Nelson et al. . | |
| 4,975,106 | 10/1990 | Ferguson .................. 71/10 |
| 5,484,729 | 1/1996 | Deweerd et al. .................. 435/262.5 |

FOREIGN PATENT DOCUMENTS

| 0181769 | 5/1986 | European Pat. Off. . |
|---|---|---|
| 0192285 | 8/1986 | European Pat. Off. . |
| 674210A5 | 5/1990 | Switzerland . |
| WO91/19039 | 12/1991 | WIPO . |
| WO92/03393 | 3/1992 | WIPO . |

OTHER PUBLICATIONS

Biosis No. 83042449, G.A. Kochkina et al "Development Of A Medium for Cultivating Entomophthora–Thaxteriana" & Biotekhnologiya, vol. 4, 1986, pp. 46–51.

Biosis #70043472, O. Yagi et al "Degradation of Poly Chlorinated Bi Phenyls by Microorganisms" & J Water Pollut Control Fed 52, vol. 5, 1980, pp. 1035–1043.

Biosis No. 70050436, M. Rusan et al "Influence of Animal Proteins on the Fermentation of Antibiotics" & Bol Col Broteriana 52, vol. 0, 1978, pp. 29–36.

*Primary Examiner*—Helen Pratt
*Attorney, Agent, or Firm*—Birch, Stewart, Kolasch & Birch

[57] ABSTRACT

Biodegradation additive characterized in that it consists of a mixture of (i) at least one assimilable nitrogen source composed of at least one unsubstituted or substituted amino acid; (ii) at least one phosphorus source, the ratio of nitrogen to phosphorus ranging from 2 to 100, said additive being subjected to a treatment to make it oleophilic. The invention also concerns an additive in accordance with any of the foregoing claims for the biodegradation of hydrocarbons.

21 Claims, 13 Drawing Sheets

OLEOPHILIC BIODEGRADING ADDITIVE AND METHOD OF TREATING HYBROCARBON POLLUTED MEDIUM

The present invention relates to a novel additive for use in bigdegradation processes, and to its application in the treatment of media polluted by hydrocarbons, by accelerating natural bigdegradation.

Numerous processes exist using microorganism cultures grown under controlled conditions (in reaction vessels for example) for subsequent use on the medium to be treated. Such processes are however ineffective when there is a requirement to operate in an outside environment. Problems are observed relating to the microorganisms becoming diluted in the natural medium, together with problems of competition with indigenous microorganisms which are much better adapted to the relevant medium. There is thus a trend towards the solution consisting in stimulating indigenous microorganisms by supplying them with elements of nutrition necessary to their development and which constitute a limiting factor in the natural medium.

Additionally, nutritional additives have been proposed for addition to the medium to be treated. Such additives can be fertilizers of the type employed in agriculture, or synthetic proteinaceous products, or yet again bacterial lyophilisates with the nutrient. These products satisfy the carbon, nitrogen and phosphorous requirements of the bacteria. The particular requirements of microorganisms for nitrogen and phosphorous correspond to an N/P molar ratio which can vary over a large range without substantial alteration in effectiveness. Apart from nitrogen and phosphorous, these additives include assimilable carbon. Such assimilable carbon is contained in hydrocarbon molecules the chain of which is similar to an aliphatic chain encountered in the hydrocarbons. Moreover, these products act as a starter, in other words they favor the very beginning of the reaction.

Availability of nutrients is also a significant problem as this determines hydrocarbon degradation kinetics. In order to speed things up, various solutions have been proposed, consisting in mixing the nutrients with various additives and forming suspensions, and particularly, emulsions. French patent 2,490,672 discloses microemulsions in which the nutrient substances are in aqueous solution which is put in microemulsion form in a lipid-miscible fluid. However, this technique implies a microemulsion-forming step and requires the presence of additives such as surfactants and others, which are expensive. French patent 2,512,057 discloses an improvement to the solution proposed to the above-cited patent, which consists in providing the source of nitrogen in a dual-system form comprising two different chemical sorts of nitrogen compounds. A preferred system is a system consisting of urea and aminated acids. Moreover, this patent teaches that aminated acids alone are not as effective as the dual system. This dual system is nevertheless a microemulsion and suffers from the same disadvantages as all (micro)emulsions.

However, there are problems over toxicity with such synthetic additives, due to the presence of derivatives such as for example, butoxyethanol, and other similar products.

Thus, one looks for natural products to use as additives; but now the problem is that these products do not contain carbon in a form which is close to an aliphatic group of the type which is present in the hydrocarbons and, because of this, are not able to set up the desired starter effect. Moreover, one looks for additives which can be employed without the need for producing a (micro)emulsion or for expensive additives.

The use of meal of animal origin is further known, this being used as a nutrient for microorganisms, the latter being in aqueous solution or suspension.

Biosis Previews Databank, Philadelphia, Biosis Number 83042449, G.A. Kochkina et al.: "Development of a Nutrient Medium for Cultivating Ntomophthora-Thaxteriana"& Biotekhnologiya, vol. 4, 1986, pages 46–51, discloses the use of fish meal as a nutrient for microorganism culture, for example Entomophthora-Thaxteriana fungi.

Biosis Previews Databank, Philadelphia, Biosis Number 70050436, M. Rusan et al.: "Influence of Animal Proteins on the Fermentation of Antibiotics"& Bol Soc Broteriana 52, vol. 0, 1978, (Recd. 1979), pages 29–36, describes the use of meat proteins or blood as a source of nitrogen for producing antibiotics from fungus-type microorganisms.

Biosis Previews Databank, Philadelphia, Biosis Number 70043472, O. Yagi et al.: "Degradation of poly-chlorinated biphenyls by microorganisms"& J. Water Pollut Control Fed 52, vol. 5, 1980, pages 1035–1043, describes the use of microorganisms for fighting pollution, meat extract being added to the culture medium.

However there is no indication that these same protein meals can also be employed in a hydrocarbon-polluted medium, in other words one that is far removed from a simple aqueous medium.

The applicant has found that, surprisingly, the additive according to the present invention meets all the requirements stated above.

Thus, the present invention provides a biodegradation-enhancing additive characterized in that it consists of a mixture comprising:

(i) at least one source of assimilable nitrogen consisting of at least one unsubstituted or substituted aminated acid;

(ii) at least one source of phosphorous;
   in a nitrogen/phosphorous (N/P) ratio of from 2 to 100; said additive having been subjected to a treatment designed to render it oleophilic.

The expression biodegradation should be taken to mean degradation by a microorganism, which is either present in situ or brought from outside. This application can hence be carried out in an outdoors medium in the presence of indigenous bacterial flora, or on the ground in the presence of a specific added bacterial flora, if the existing flora is considered insufficient.

The microorganism employed can be a yeast, a fungus or a bacteria; in fact, any microorganism able to break down a hydrocarbon is appropriate. The following can be cited by way of non-limiting examples: Pseudomonas, Acitenobacter, Flavobacterium, Artrobacter, Corynebacterium.

Assimilable nitrogen should be taken to mean nitrogen that is effectively metabolized by the microorganism during degradation.

The stated treatment, which has the aim of rendering the additive oleophilic (i.e. having an affinity for oils), can be a conventional treatment. The following can be cited as examples: acylation, esterification, grafting of a long radical onto various groups, a Schiff base transformation, carbamate formation in the presence of isocyanate, and others. Preferably, the treatment consists of acylation. The carbon chain of the acyl group is preferably a fatty acid chain; advantageously, an acid chloride is employed, particularly of laurylic acid.

Aminated acids able to be employed in the framework of the present invention can consist of any aminated acid, whether natural or consisting of closely related synthetic acids such as ornithine, and others. These aminated acids can be substituted or unsubstituted. When they are substituted, the substituent can be an alkyl, lower alcoxy or hydroxy group, and others as well. Preferably, the aminated acid is selected from the group comprising lysin, methionine, cystine, threonine, tryptophan, hydroxylysin, hydroxyproline, and mixtures thereof.

Preferably, the source of assimilable nitrogen makes up at least 5% by weight of the total weight of said biodegradation additive.

In one embodiment, the source of assimilable nitrogen is found in proteins which represent at least 50% by weight of the total weight of the said additive.

Any source of phosphorous, whether natural or synthetic, is appropriate. The preferred source of phosphorous is a mineral salt of phosphorous.

The said N/P ratio is advantageously comprised between 4 and 40 and is preferably equal to about 16.

In one embodiment of the invention, the additive is an animal meal.

The meal can be a fish meal, or alternatively it can be a meal obtained from meat.

Fish and meat meals are obtained by any conventional manufacturing method. By way of example, the following process can be cited for the production of meat meal: cutting up of animal carcasses followed by milling, size grading, pre-heating, draining, drying, pressing and final milling. The following process can be cited as typical of the production of fish meal: cutting up and cooking the fish product and pressing it, mixing it with a concentrate of liquid from pressing, and then drying, size-grading and finally milling it.

The composition of such meals can vary over a wide range; by way of example the following can be provided as examples which are representative but non-limiting of the compositions for various meals:

Fish meal:
proteins: 60 to 85%
   including the main aminated acids: lysin, methionine, threonine.
fatty matter: 3 to 25%.
inorganic matter (phosphorous, calcium, chlorides): 5 to 24%, Meat meal:
proteins: 60 to 85%
including the main aminated acids: lysin, threonine, hydroxyproline.
fatty matter: 2 to 7%.
inorganic matter (phosphorous, calcium, chlorides): 7 to 28%.

The use of additives according to the present invention, such as meat or fish meals, is hence useful for biodegradation of hydrocarbons on the ground, in sediments and on the surface of water. Sediments polluted by hydrocarbons can originate from accidental or non-accidental hydrocarbon spill-age, such as the cleaning of tanks, highways, land, etc. This use is just as suitable and profitable in the case of treatment in enclosed media such as reaction vessels, waste pits, hydrocarbon storage vessels, and so on.

The hydrocarbon-to-additive ratio is variable. The weight ratio of additive/hydrocarbons is generally comprised between 3 and 30. Preferably, the weight ratio is about 10.

The present invention also covers the use of the present additives for biodegradation of hydrocarbons.

The following examples illustrate the invention in more detail, without however limiting it.

EXAMPLES

Composition of additives
The composition of the biodegradation additives is given in the table below.

| Products | % Nitrogen (N) | % Phosphorous (P) | N/P | % Carbon (C) |
|---|---|---|---|---|
| fish meal (Solatlante G) | 12.1 | 0.6 | 20.2 | 50.1 |
| meat meal: 60% (Viandor extraction) | 9.8 | 3.95 | 2.5 | 35.4 |
| meat meal: 70% (Viandor extraction greaves) | 12.0 | 3.1 | 3.9 | 40.8 |
| meat meal: 80% (Viandor extraction greaves) | 12.9 | 1.4 | 9.2 | 40.5 |

| | FISH | MEAT 60% | MEAT 70% | MEAT 80% |
|---|---|---|---|---|
| PROTEINS | 70–73 | 60 | 70 | 80 |
| Lysin | 5.20 | 3.25 | 4.20 | 4.86 |
| Methionine | 2.05 | 0.85 | 1.00 | 1.20 |
| Cystine | 0.55 | 0.85 | 0.42 | 0.48 |
| Threonine | 2.65 | 2.00 | 2.40 | 2.75 |
| Tryptophan | 0.70 | 0.45 | 0.70 | 1.10 |
| Hydroxylysin | — | 0.45 | 0.42 | 0.48 |
| Hydroxyproline | — | 3.42 | 3.85 | 4.40 |
| MOISTURE | 3–5 | 4–9 | 3–7 | 3–7 |
| FATTY MATTER | 20–23 | 2–6 | 2–4 | 2–4 |
| INORGANIC MATTER | 5–7 | 25–28 | 17–20 | 7–10 |
| Phosphorous | 0.40–0.80 | 3.5–4.2 | 2.9–3.3 | 1.2–1.6 |
| Calcium | 0.15–0.50 | 7–9 | 5.5–7.0 | 2.4–3.7 |
| Chlorides (NaCl) | 2–3 | 1.4–1.6 | 1.1–1.5 | 0.8–1.0 |

Their average analytical composition was as follows:
The present invention is illustrated in greater detail in the examples that follow which should be considered as illustrative but not limiting.

EXAMPLE 1

Figure 2:
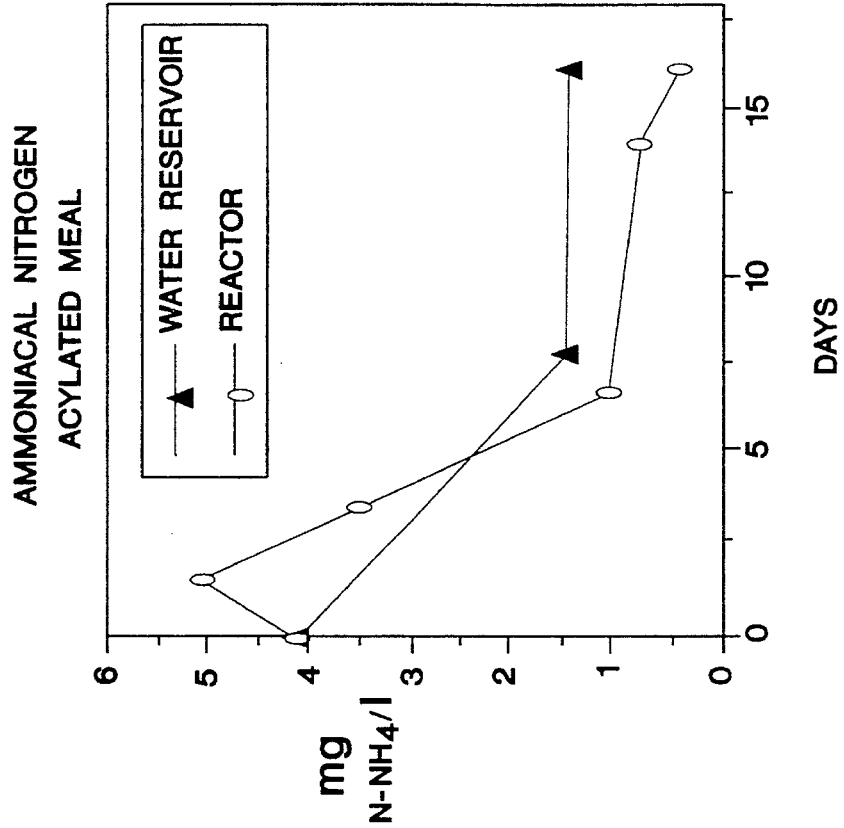
FIGS. 1 and 2 show the evolution of ammoniacal nitrogen in reservoirs and reactors when the meal has and has not been acylated.
Figure 1:
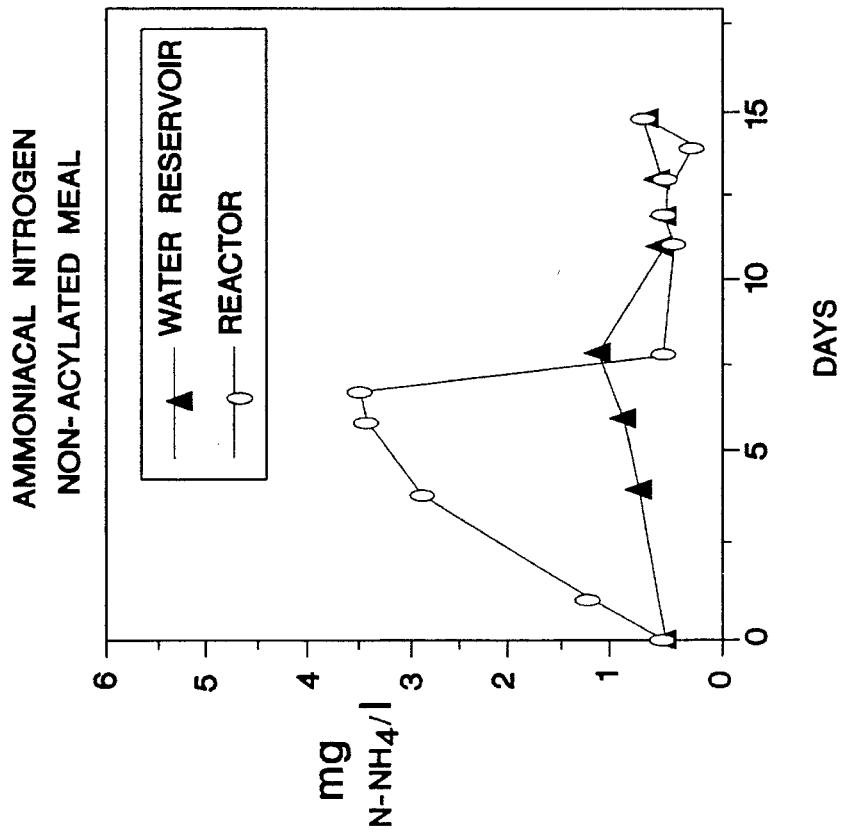
Figure 3:
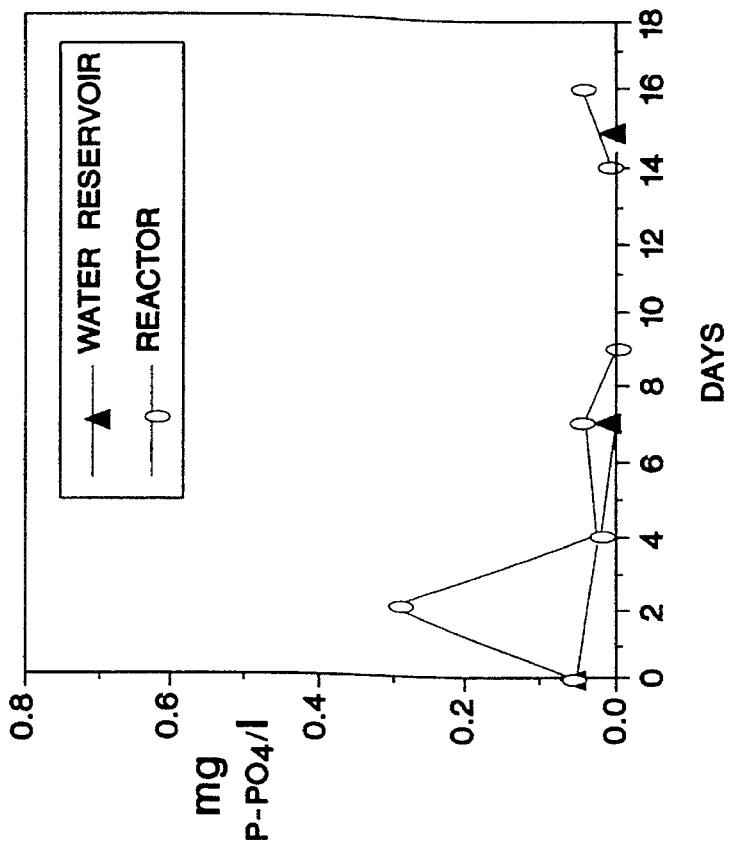
FIGS. 3 and 4 show the evolution of orthophosphate content in reservoirs and reactors when the meal has and has not been acylated.
Figure 4:
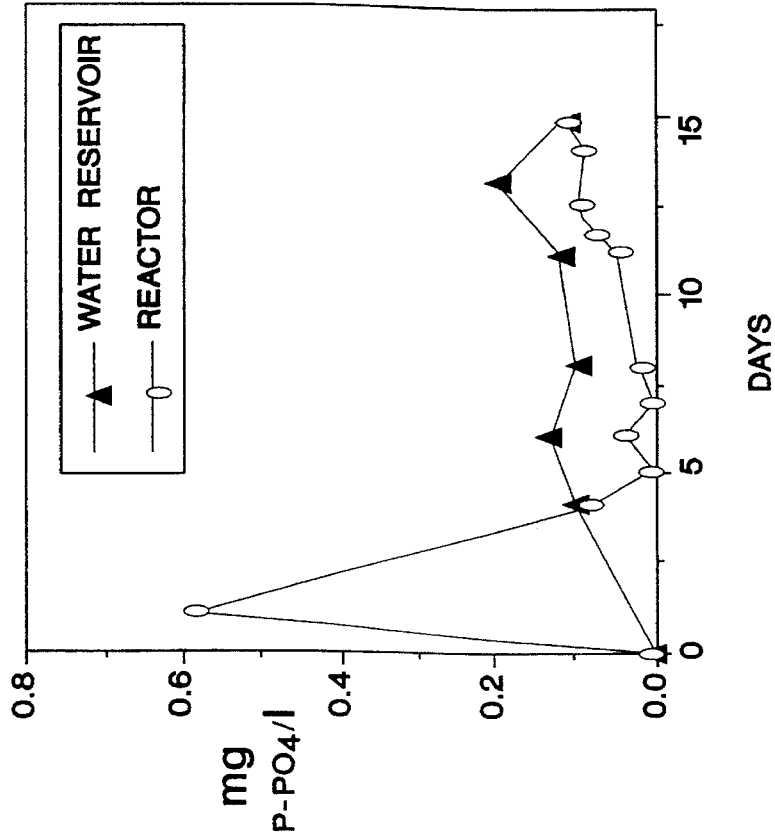
Figure 5:
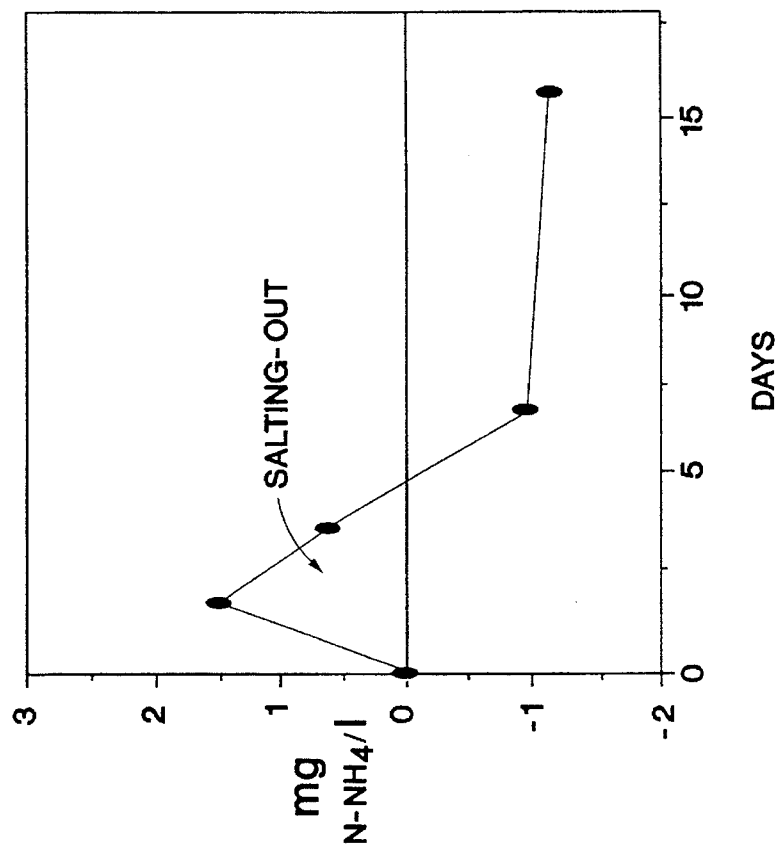
FIGS. 5 and 6 show the salting-out of nitrogen in reactors when the meal has and has not been acylated.
Figure 6:
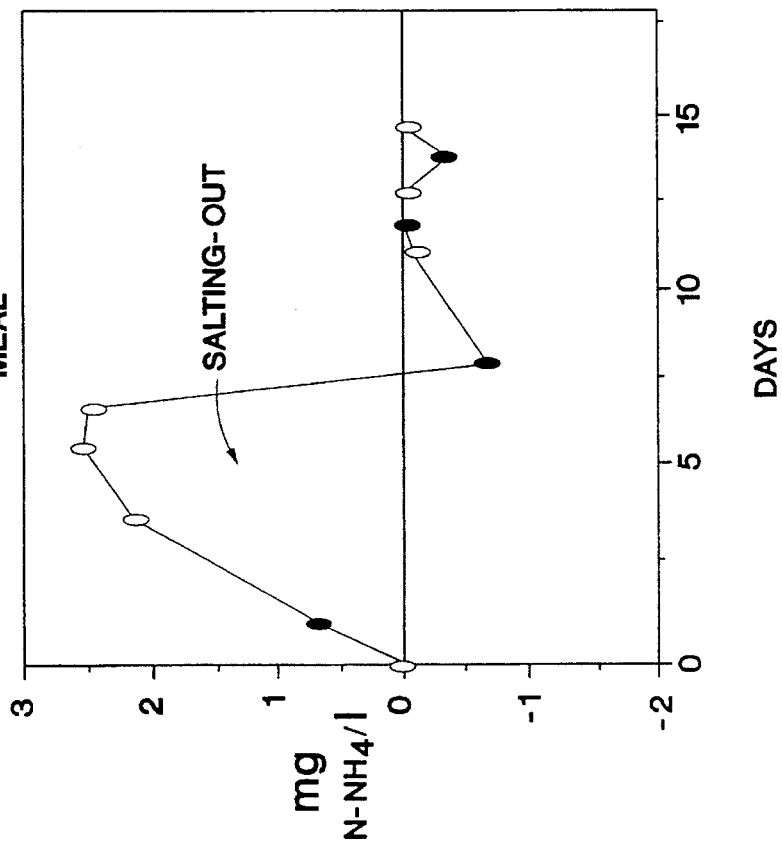
Figure 7:
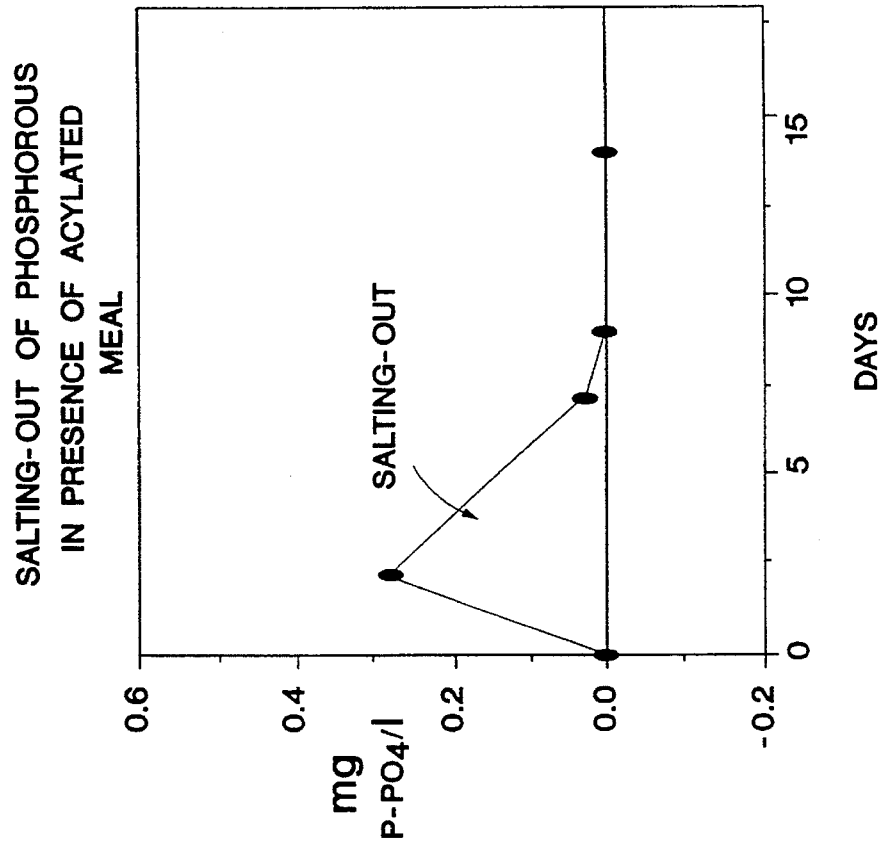
FIGS. 7 and 8 show the salting-out of phosphorous in reactors when the meal has and has not been acylated.
Figure 8:
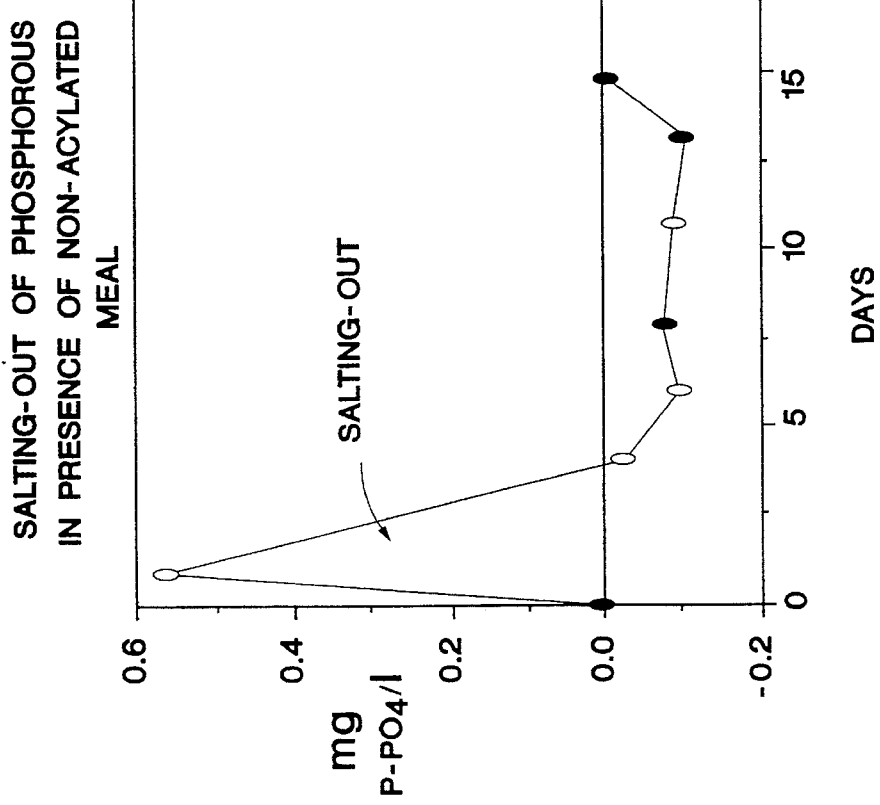

Biodegradation of hydrocarbons in the presence of acylated animal meals.

In order to render animal meals more oleophilic, crude meals were subjected to an acylation reaction.

Synthesis of acylated meal.

Synthesis of the acylated meal was obtained under the conditions described below.

Synthesis was carried out in a solvent medium.

This reaction was based on bringing animal meal (fish meal) into contact with an acid chloride (lauryl chloride $C_{12}H_{23}C_{10}$) in the presence of a solvent (dichloromethane $CH_2C_2$). A proton acceptor consisting of triethylamine $[(C_2H_5)_3N]$ was added to the medium.

In a reaction vessel, the mixture consisting of lauryl chloride, fish meal, dichloromethane and triethylamine was agitated (mechanical agitation) for 24 hours at 30° C.

An excess amount of acid chloride (+20%) over that amount necessary to react on the amine groups of the lysin was employed. Lysin represents some 5% of the fish meal proteins. The amount of triethylamine was added in the same proportions.

After reacting for 24 hours, the acylated meal was washed over a filter with a solvent (dichloromethane) to eliminate excess acid chloride. The cake was then redissolved in water and filtered to eliminate excess triethylamine and the salt formed. The cake consisting of the acylated meal was then kiln dried.

First test (Extent of oleophilic nature of acylated meal).

The extent of the oleophilic nature of crude meal or acylated meal was measured using a distribution coefficient test.

A mixture of nitrogen-free artificial seawater (700 ml) + hydrocarbons (Arabian light crude BAL 150: 28g) and a known amount of animal meal on the surface of the hydrocarbons was agitated for 5 minutes in a separating funnel. After agitation, decantation was allowed to proceed for 12 hours and the nitrogen content of the aqueous phase was measured. This nitrogen content is a reflection of how much of the nitrogen contained in the meal has passed into the aqueous phase. It is thus possible to calculate how oleophilic the meal is. Table I below gives the results obtained.

In order to test the effectiveness of animal meals in hydrocarbon biodegradation, a scintillometric measurement technique was used with a radioactive hydrocarbon (hexadecane) model. It is possible to follow biodegradation by monitoring $14_{CO2}$ production in line with the following principle: In order to follow the breakdown kinetics of the marked substrate the amount of $^{14}CO_2$ released by a bacterial culture was observed. A technique employing a minireactor (5 ml) was used for this, the reactor containing a bacterial culture (nutrient medium: 1 ml and inoculum: 0.1 ml), the reactor being enclosed in a scintillation flask containing 2.5 ml molar soda. After incubation at 20° C. in darkness and without agitation the amount of $^{14}CO_2$ trapped in the soda was analyzed after acidifying the culture medium and after adding a scintillation liquid (Hionic fluoride). The same applied to the marked substrate remaining in the flask. Radioactivity was read on a Beckmann Instruments LS 3801 scintillation counter.

Table II below gives the results obtained.

TABLE II

Biodegradation (%) of hexadecane with and without the presence of acylated and non-acylated meal

| Time (days) | Hexadecane | Raw meal | Acylated meal |
|---|---|---|---|
| 0 | 0.3% | 0.0% | 0.1% |
| 4 | 0.0% | 2.2% | 45.9% |
| 10 | 0.0% | 9.1% | 13.1% |
| 20 | 0.0% | 4.4% | 33.0% |

The biodegradation rate of hexadecane alone remained at 0. The bacteria present are not then capable of degrading hexadecane as such. However, in the presence of animal meal acceleration of hexadecane biodegradation was observed. Acceleration was more pronounced when the meal was acylated.

EXAMPLE 2

Biodegradation of hydrocarbons in the presence of acylated or non-acylated animal meal, in an outdoor medium In order to demonstrate the value of rendering animal meals oleophilic, tests were carried out in an outdoor medium to verify if the oleophilic nature of the meal made it possible to maintain the nutrient elements (nitrogen and phosphorous) in contact with the hydrocarbons thus speeding up biodegradation.

Acylation of fish meal

The animal meals employed for examples 2 and 3 were fish meals. The following modifications were made to

TABLE I

Extent of oleophilic nature of animal meals: (HC: hydrocarbons. N: nitrogen)

| Animal meal | meal/HC weight % | % of N in meal | Amount of nitrogen introduced | Amount of nitrogen in the water | % of nitrogen in the water |
|---|---|---|---|---|---|
| Raw meal | 3.54% | 12.1% | 120 mg | 123.9 mg | 100.0% |
| Acylated meal | 3.54% | 12.1% | 120 mg | 3.5 mg | 2.9% |

It can thus be observed that subjecting the animal meal to acylation treatment renders the meal oleophilic and that salting-out of nitrogen drops off distinctly when the meal has been acylated.

Second test (hydrocarbon biodegradation in the presence of acylated or non-acylated meal).

chemical synthesis compared with what is described above for example 1:

reaction temperature: this was of the order of 50° C, corresponding to the solvent reflux temperature, the duration of the reaction was 17 hours, the acid chloride was in excess by 300% in correspondence to the parameter which underwent the biggest modification compared to the synthesis in example 1. The other parameters and test procedures were unchanged.

Test:

The test setup used in this series of experiments consisted of a reactor containing 100 ml of hydrocarbon-polluted (with 2.5 ml light Arabian) sea water. The acylated or non-acylated animal meal was applied to the surface of the hydrocarbon in an amount of 10% by weight on the basis of the amount of hydrocarbon present. The reactor was continuously agitated and aerated. The water in the reactor was renewed continuously during the 15 days with sea water contained in a reservoir, 8 renewals being performed per day. The effluent was collected at the outlet from the reactor and physical-chemical analyses ($NH_4$; $NO_3$ $PO_4^{3-}$ hydrocarbons) and bacteriological analyses (total and specific bacteria) were carried out. These same analyses were performed on the water in the reservoir. At the end of the test, the complete reactor was sacrificed and the remaining hydrocarbons were extracted using chloroform.

The physical-chemical analyses were carried out using the applicable standards: AFNOR NF T90-015 for ammoniacal nitrogen, standard methods 4500-NO3-E for nitrogen in nitrate form, standard method 4500-PC-Vn Acid Col. Meth. for orthophosphate.

Total bacteria were counted using the most probable number method, in a liquid medium (Marine Broth 2216). Hydrocarbon-specific bacteria were also counted using the most probable number technique in a liquid medium, in which the hydrocarbons represent the only source of carbon. The hydrocarbons were analysed by gaseous phase chromatography.

Two tests were done: one with non-acylated animal meal and the other with the same animal meal, but acylated this time. Each test lasted 15 days. The results obtained are given below. The evolution of the mineral elements ($NH_{4+}$; $PO_4^{3-}$) are given in tables III and IV and in FIGS. 1, 2, 3 and 4.

TABLE III

Evolution of ammoniacal nitrogen content in the two tests: acylated and non-acylated meal

| N—NH4+ Days | NON-ACYLATED MEAL | | ACYLATED MEAL | |
|---|---|---|---|---|
| | Reservoir mg/l | Reactor mg/l | Reservoir mg/l | Reactor mg/l |
| 0 | 0.50 | 0.50 | 4.00 | 4.00 |
| 1 | 0.52 | 1.20 | | |
| 2 | | | 3.50 | 5.00 |
| 4 | 0.75 | 2.90 | 2.85 | 3.50 |
| 6 | 0.90 | 3.40 | | |
| 7 | 1.025 | 3.50 | 2.00 | 1.10 |
| 8 | 1.15 | 0.50 | 1.50 | |
| 11 | 0.50 | 0.40 | | |
| 12 | 0.50 | 0.50 | | |
| 13 | 0.50 | 0.49 | | |
| 14 | 0.625 | 0.25 | | 0.80 |
| 15 | 0.75 | 0.75 | | |
| 16 | | | 1.48 | 0.45 |

TABLE IV

Evolution of orthophosphate content in the two tests: with acylated and non-acylated meal

| P—$PO_4^{3-}$ Days | NON-ACYLATED MEAL | | ACYLATED MEAL | |
|---|---|---|---|---|
| | Reservoir mg/l | Reactor mg/l | Reservoir mg/l | Reactor mg/l |
| 0 | 0.00 | 0.00 | 0.05 | 0.05 |
| 1 | 0.025 | 0.59 | | |
| 2 | | | 0.025 | 0.30 |
| 4 | 0.10 | 0.08 | | 0.02 |
| 5 | | 0.00 | | |
| 6 | 0.125 | 0.03 | | |
| 7 | | 0.00 | 0.00 | 0.03 |
| 8 | 0.10 | 0.025 | | |
| 9 | | | 0.00 | 0.00 |
| 11 | 0.13 | 0.04 | | |
| 12 | | 0.09 | | |
| 13 | 0.20 | 0.10 | | |
| 14 | | 0.085 | 0.00 | 0.00 |
| 15 | 0.110 | 0.110 | 0.00 | |
| 16 | | | | 0.04 |

The results obtained differed for acylated and non-acylated meal. It can be observed that the acylated meal produced less salting-out of the nitrogen and phosphorous. Account should be taken of the comparison between nitrogen and phosphorous concentrations in the water in the reservoir which were varying as this was "living" (plancton, bacteria, etc. . .) seawater. Availability of these results thus made it possible to estimate what amount of nutrient had been eliminated by subtraction with the concentrations measured in the reservoirs. The results are given in table V and in FIGS. 5, 6, 7 and 8.

TABLE V

Salting-out of nutrient: nitrogen and phosphorous in each reactor: with acylated and non-acylated meal

| Days | AMMONIACAL NITROGEN | | PHOSPHATE | |
|---|---|---|---|---|
| | Non-acylated meal | Acylated meal | Non-acylated meal | Acylated meal |
| 0 | 0.000 | 0.000 | 0.000 | 0.000 |
| 1 | 0.680 | | 0.565 | |
| 2 | | | | 0.275 |
| 4 | 2.150 | 1.500 | −0.020 | |
| 5 | | 0.650 | | |
| 6 | 2.500 | | −0.095 | |
| 7 | 2.475 | −0.900 | | 0.030 |
| 8 | −0.650 | | −0.075 | |
| 9 | | | | 0.000 |
| 10 | | | | |
| 11 | −0.100 | | −0.090 | |
| 12 | 0.000 | | | |
| 13 | −0.010 | | −0.100 | |
| 14 | −0.375 | | | 0.000 |
| 15 | 0.000 | | 0.000 | |
| 16 | | −1.030 | | |

Figure 9:
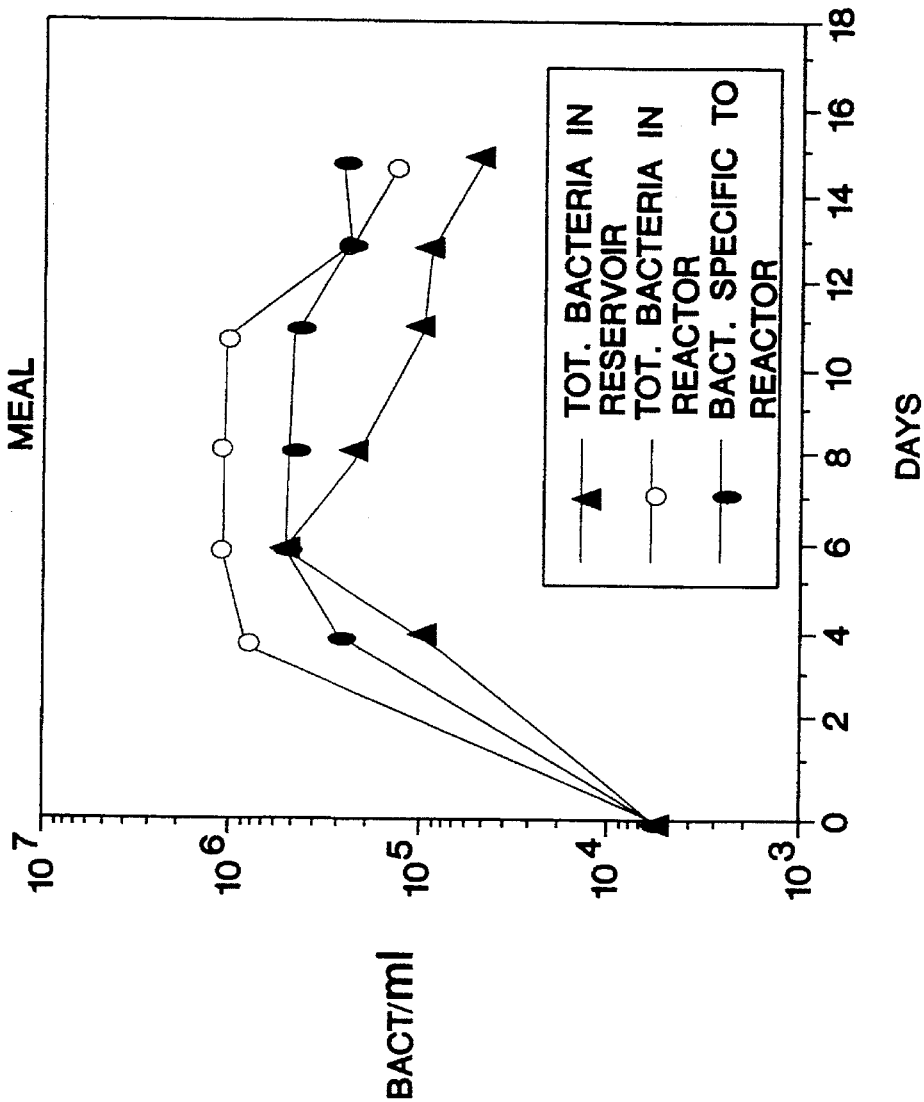
FIGS. 9 and 10 show the development over time of total and hydrocarbon-specific bacterial flora in the presence of non-acylated meal and acylated meal.
Figure 10:
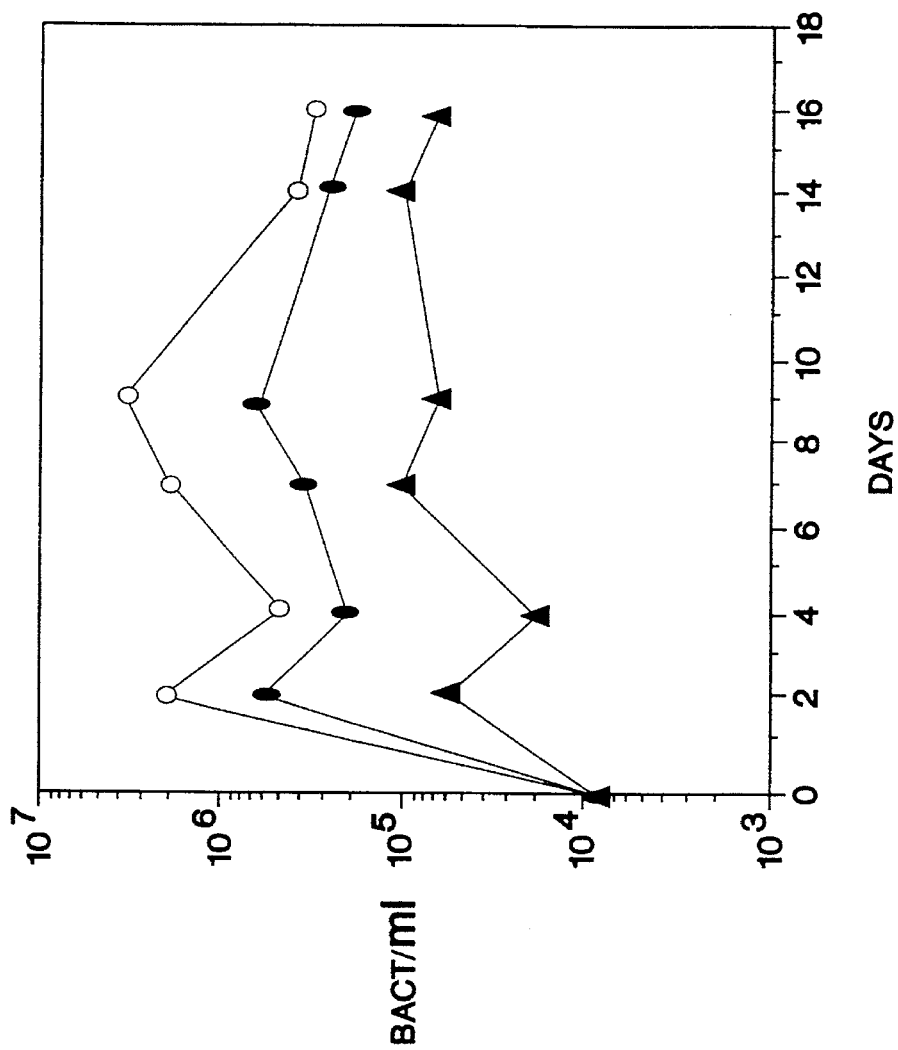
Figure 11:
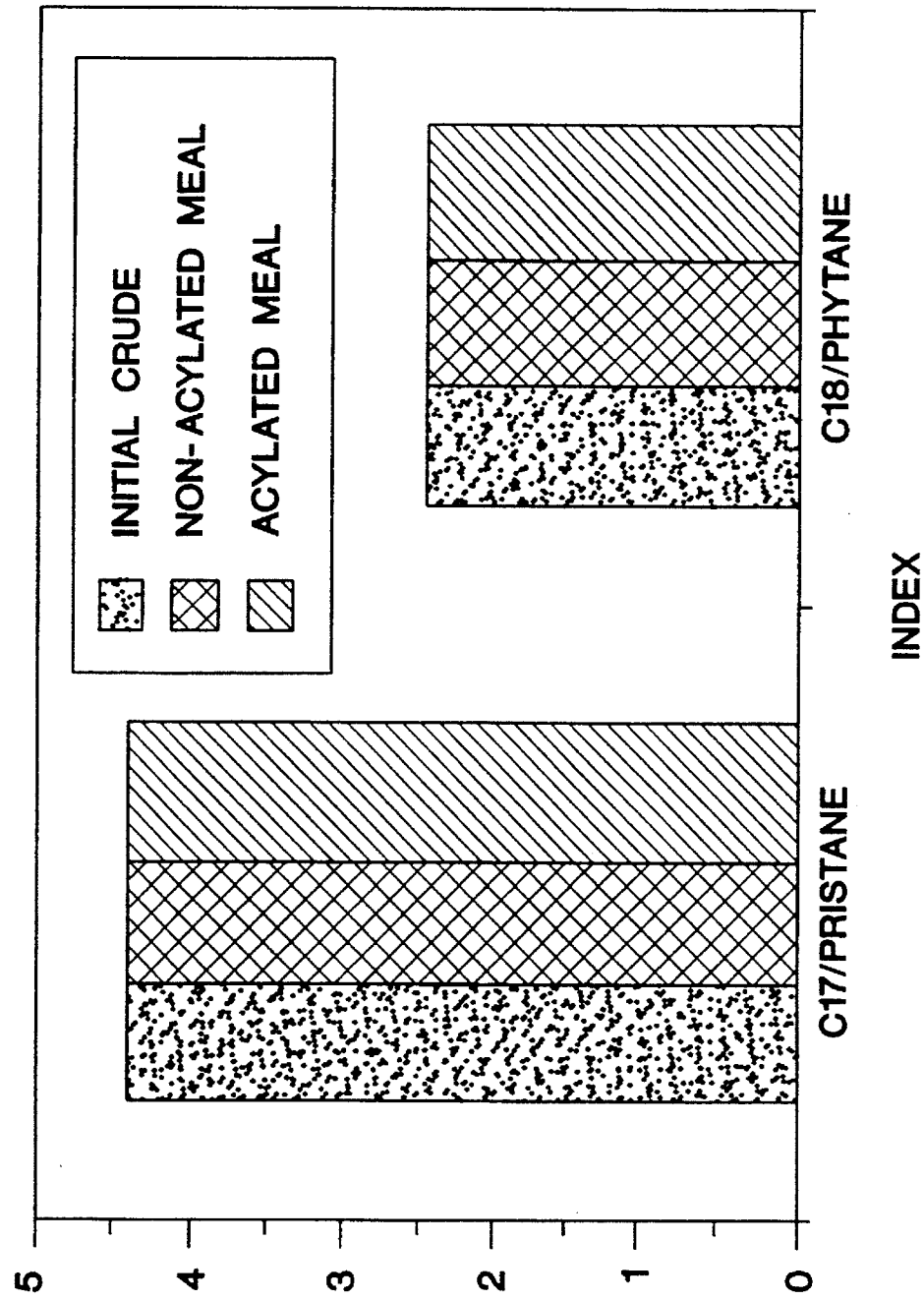
FIG. 11 shows the evolution of biodegradation index of alkanes for two tests: one in the presence of acylated meal and the other in the presence of non-acylated meal.

These results clearly show that salting-out was much less pronounced for the meal rendered oleophilic by acylation. This treatment thus makes it possible to attain a product that spends more time in contact with the hydrocarbon. Thus, those nutrients— nitrogen and phosphorous— that are indispensable to hydrocarbon-specific bacterial development are present at the place where biodegradation is occurring, in other words at the water-hydrocarbon interface. The results concerning bacterial flora evolution are given in table VI and VII, and in FIGS. 9 and 10.

TABLE VI

Total and hydrocarbon-specific bacterial flora evolution
in reactor with non-acylated meal

| | RESERVOIR | REACTOR | |
|---|---|---|---|
| Days | Total bacteria Bact/ml | Total bacteria Bact/ml | Specific bacteria Bact/ml |
| 0 | $5 \cdot 10^3$ | $5 \cdot 10^3$ | $5 \cdot 10^3$ |
| 2 | | | |
| 4 | $8 \cdot 10^4$ | $8 \cdot 10^5$ | $2.4 \cdot 10^5$ |
| 6 | $5 \cdot 10^5$ | $1.1 \cdot 10^6$ | $5 \cdot 10^5$ |
| 7 | | | |
| 8 | $2.2 \cdot 10^5$ | $1.1 \cdot 10^6$ | $5 \cdot 10^5$ |
| 9 | | | |
| 11 | $1 \cdot 10^5$ | $1.1 \cdot 10^6$ | $5 \cdot 10^5$ |
| 13 | $8 \cdot 10^4$ | $2.4 \cdot 10^5$ | $2.4 \cdot 10^5$ |
| 14 | | | |
| 15 | $5 \cdot 10^4$ | $1.3 \cdot 10^5$ | $2.6 \cdot 10^5$ |
| 16 | | | |

TABLE VII

Total and hydrocarbon-specific bacterial flora evolution
in reactor with acylated meal

| | RESERVOIR | REACTOR | |
|---|---|---|---|
| Days | Total bacteria Bact/ml | Total bacteria Bact/ml | Specific bacteria Bact/ml |
| 0 | $8 \cdot 10^3$ | $8 \cdot 10^3$ | $8 \cdot 10^3$ |
| 2 | $5 \cdot 10^4$ | $2.2 \cdot 10^6$ | $8 \cdot 10^5$ |
| 4 | $2.2 \cdot 10^4$ | $5 \cdot 10^5$ | $2.4 \cdot 10^5$ |
| 6 | | | |
| 7 | $1.2 \cdot 10^5$ | $2.6 \cdot 10^6$ | $5 \cdot 10^6$ |
| 8 | | | |
| 9 | $8 \cdot 10^4$ | $5 \cdot 10^6$ | $1 \cdot 10^6$ |
| 11 | | | |
| 13 | | | |
| 14 | $1.2 \cdot 10^5$ | $5 \cdot 10^5$ | $3 \cdot 10^6$ |
| 15 | | | |
| 16 | $9 \cdot 10^4$ | $4 \cdot 10^5$ | $2.2 \cdot 10^5$ |

Bacterial counts carried out during the two tests made it possible to bring to light the fact that, in the case of the acylated meal, bacterial development was not only faster, but, above all, showed how much difference there was in the number of bacteria found in the reservoir (which entered the reactor every day) this being higher in the presence of the meal. The latter thus has a favorable stimulating effect on total and hydrocarbon-specific bacteria, as the nutrients are more available.

Hydrocarbon biodegradation quantification was carried out by estimating a biodegradation index calculated starting from gaseous-phase chromatography. These indexes are the C17/pristane and C18/phytane ratios. The decrease of these ratios is correlated to the biodegradation of the aliphatic hydrocarbons. The ratios are given in table VIII.

TABLE VIII

Degree of biodegradation obtained
after 15 days

| | NON-ACYLATED MEAL | | ACYLATED MEAL | |
|---|---|---|---|---|
| Days | C17/ pristane | C18/ phytane | C17/ pristane | C18/ phytane |
| 0 | 4.4 | 2.5 | 4.4 | 2.5 |
| 15 | 4.4 | 2.5 | 3.8 | 2.3 |

The results, in particular the evolution of biodegradation indexes demonstrate that the acylated meal gave better results than the non-acylated meal.

The results make it possible to state that the acylation of the animal meal leads to a product that stays in contact with the hydrocarbons: nitrogen and phosphorous are present at the water-hydrocarbon interface and this stimulates the bacterial flora, whether this be specific or total, and hydrocarbon biodegradation resulting therefrom is also stimulated.

Acylated animal meal thus has an advantage over non-acylated meal in speeding up hydrocarbon biodegradation.

EXAMPLE 3

Biodegradation of hydrocarbons in the presence of acylated and non-acylated animal meal carried out outdoors on a large scale In view of the results of the laboratory experiments which showed the value of employing an acylated animal meal, a trial on a much larger scale was carried out. The trial was done on 3 tanks of 400 liters capacity continuously supplied with fresh seawater pumped from a lagoon situated next to the tanks. The renewal rate of the water in the tanks was 4 times their volume per day. Oil (Arabian light topped at 150° C.) was introduced into each tank (1 liter). One tank was kept as a control and no oil was introduced; non-acylated meal (5%/crude) was added to the second tank; acylated meal (5%/crude) was added to the third tank. The non-acylated and acylated meal was identical to that used in example 2.

Throughout the experiments, which lasted 2 months, total and hydrocarbon-specific bacterial flora was studied using the same test procedure as the one described for example 2. The hydrocarbons were also followed permanently.

Figure 13:
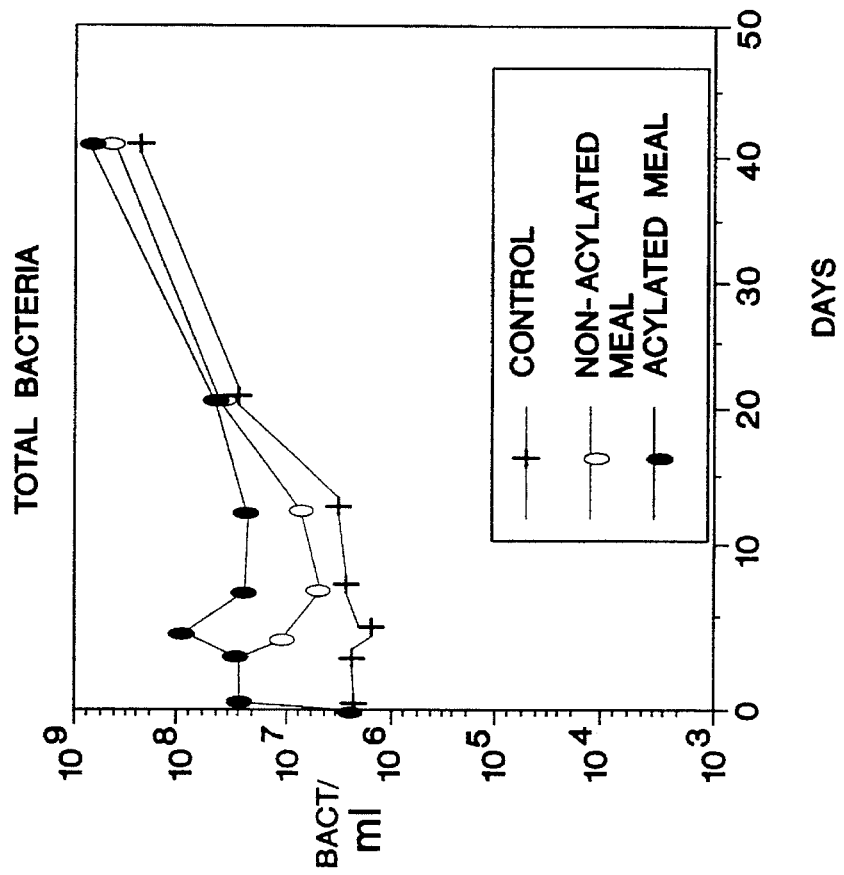
FIGS. 12 and 13 show the development over time of total and hydrocarbon-specific bacterial flora in three ponds, one acting as a control, the others in the presence of acylated and non-acylated meal.
Figure 12:
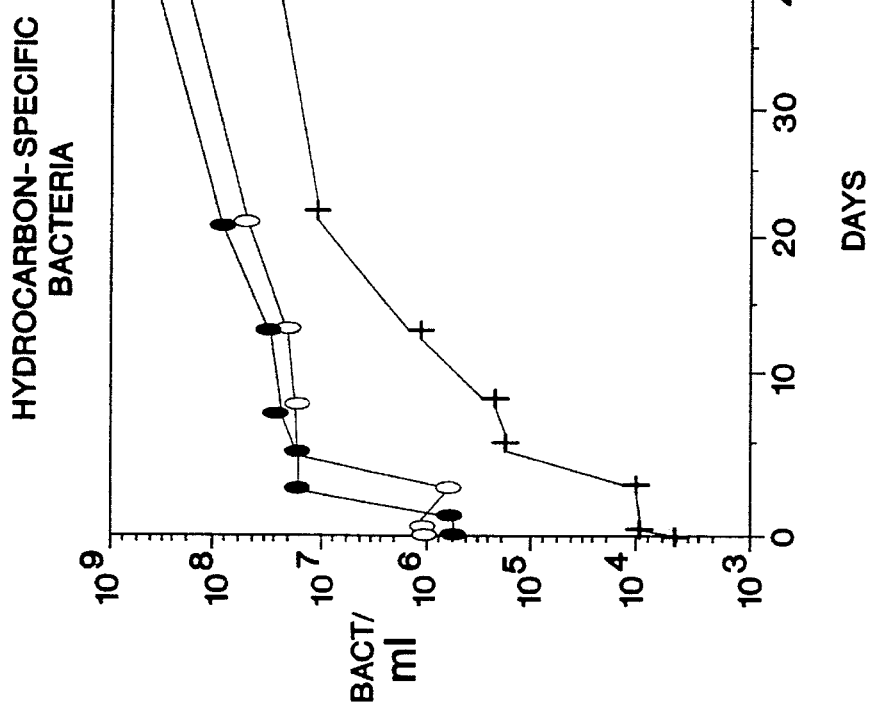

The results of the bacteriological studies are given in table IX and in FIGS. 12 and 13.

TABLE IX

| | Total and specific bacteria count in hydrocarbons | | | | | |
|---|---|---|---|---|---|---|
| | Total bacteria Bact./ml | | | Specific bacteria Bact./ml | | |
| Days | Control | Non-acylated meal | Acylated meal | Control | Non-acylated meal | Acylated meal |
| 0  | 2.4E + 06 | 2.4E + 06 | 2.4E + 06 | 4.6E + 03 | 1.1E + 06 | 4.6E + 05 |
| 1  | 2.4E + 06 | 2.4E + 07 | 2.4E + 07 | 1.1E + 04 | 1.1E + 06 | 4.6E + 05 |
| 3  | 2.4E + 06 | 2.4E + 06 | 2.4E + 06 | 1.1E + 04 | 4.6E + 05 | 1.4E + 07 |
| 5  | 1.5E + 06 | 9.3E + 06 | 9.3E + 07 | 1.4E + 05 | 1.4E + 07 | 1.4E + 07 |
| 8  | 2.3E + 06 | 4.0E + 06 | 2.3E + 06 | 1.8E + 05 | 1.6E + 07 | 2.0E + 07 |
| 14 | 3.1E + 06 | 6.9E + 06 | 2.3E + 07 | 1.8E + 06 | 2.0E + 07 | 2.8E + 07 |
| 22 | 2.5E + 07 | 3.9E + 07 | 4.3E + 06 | 1.4E + 07 | 4.6E + 07 | 7.9E + 07 |
| 42 | 2.5E + 08 | 4.6E + 08 | 6.3E + 07 | 2.4E + 07 | 2.4E + 08 | 5.0E + 08 |

In the tanks treated with acylated or non-acylated meal, bacterial flora development was more pronounced than in the control. The animal meals thus had a stimulating effect on indigenous bacterial flora.

It was observed that development was greater in the tank treated with acylated meal than in the tank treated with non-acylated meal. Acylation of the meal makes it possible to keep the product close to the hydrocarbon layer thus favoring bacterial flora development.

Figure 14:
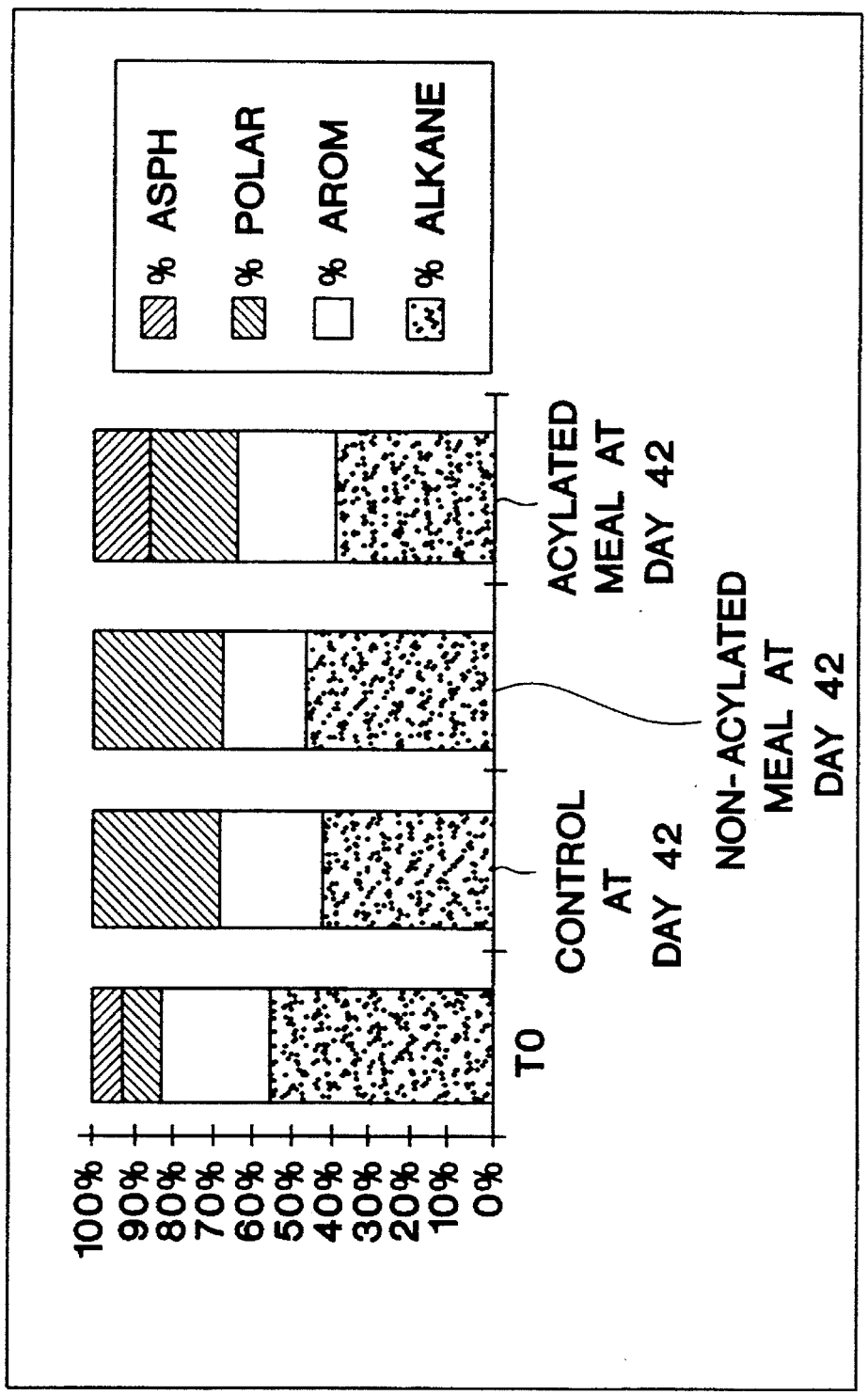
FIG. 14 shows the composition of samples of crude recovered from the three ponds at time 0, and after 42 days, showing the alkane, aromatic, asphaltene and resin fractions.
Figure 15:
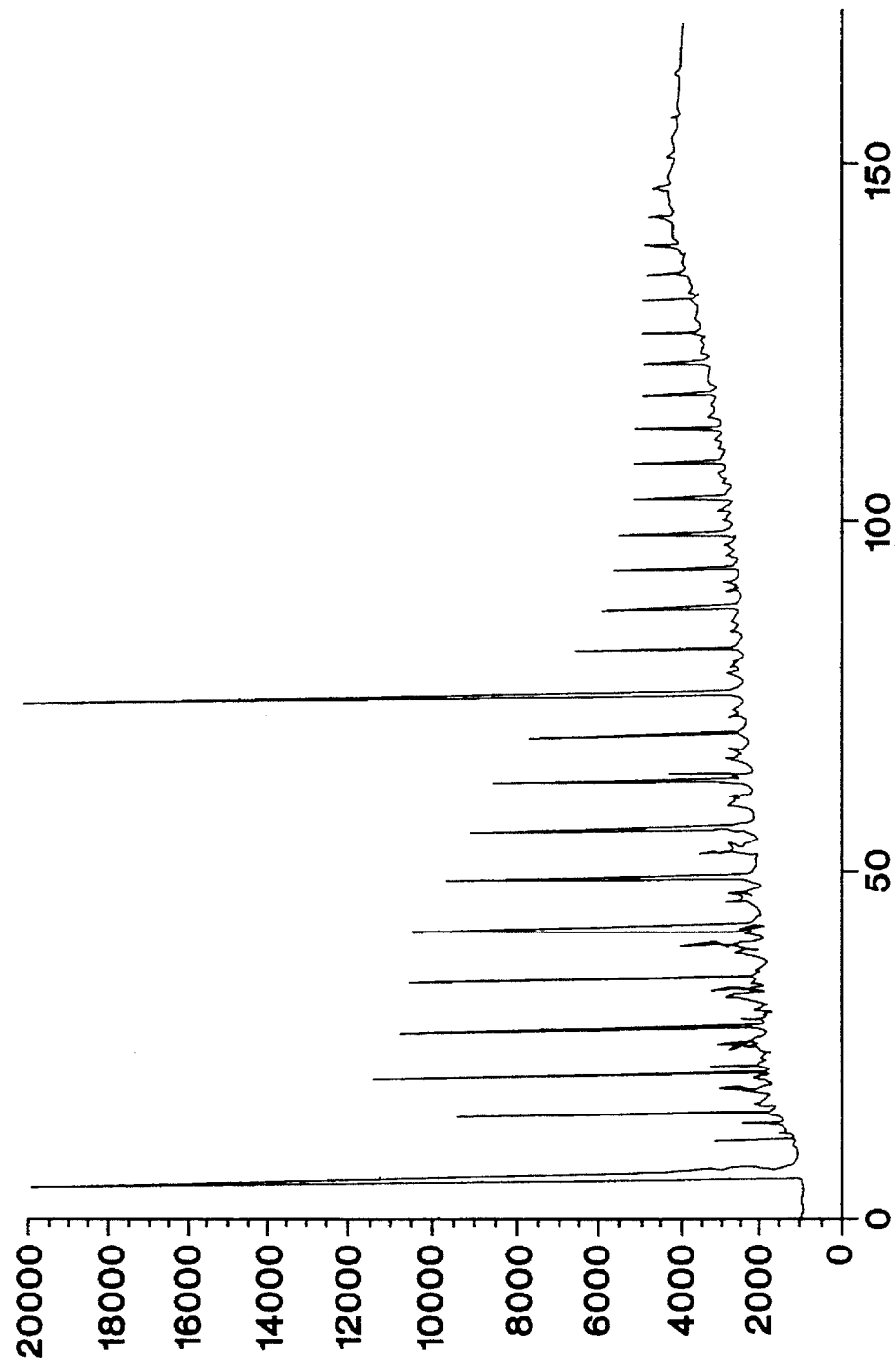
FIGS. 15 to 18 are chromatograms of the alkane fraction for, respectively, Arabian light crude BAL 150 at day 0, the control pond after 42 days, the pond treated with non-acylated meal after 42 days and the pond treated with acylated meal after 42 days.
Figure 16:
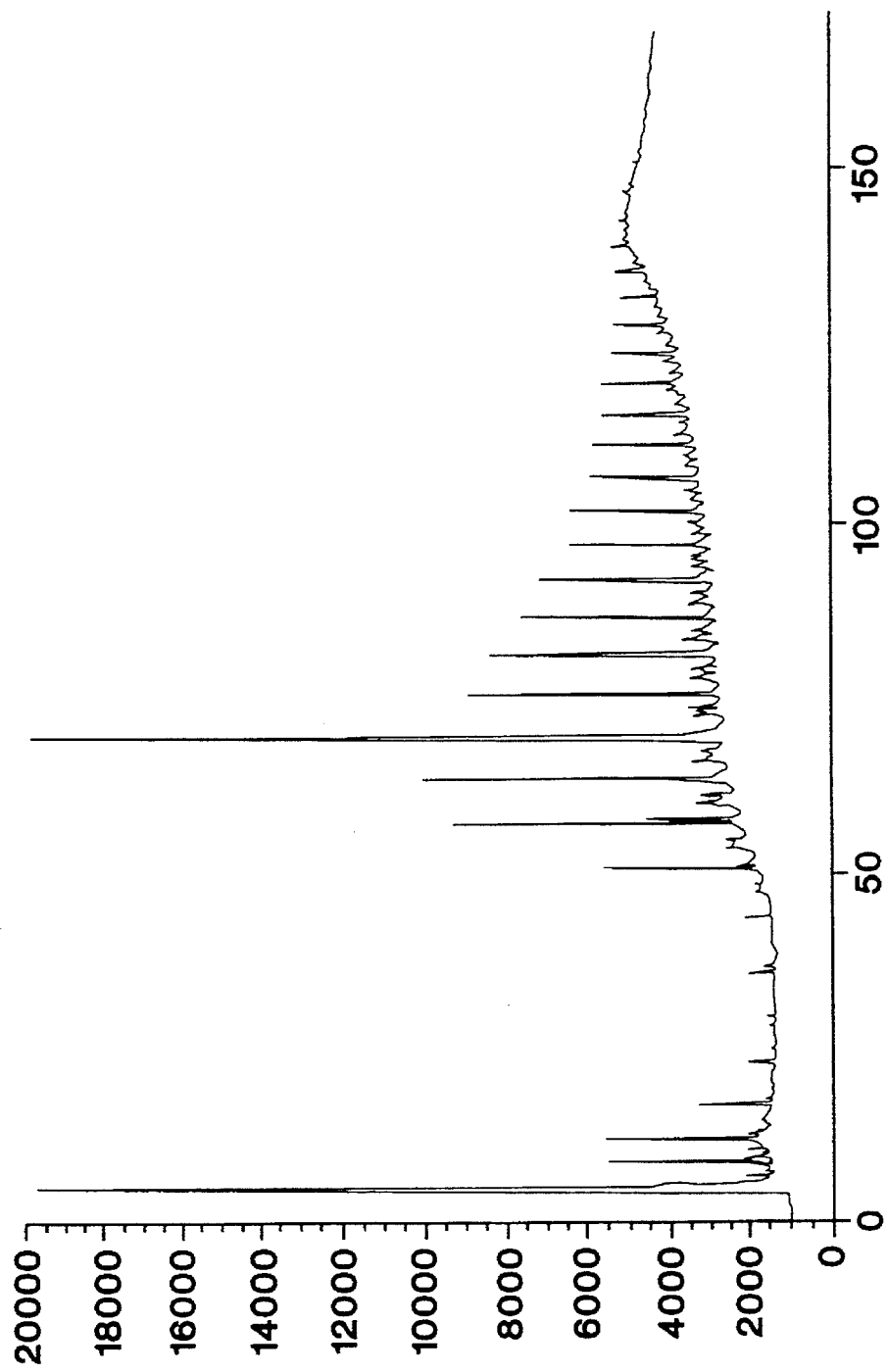
Figure 17:
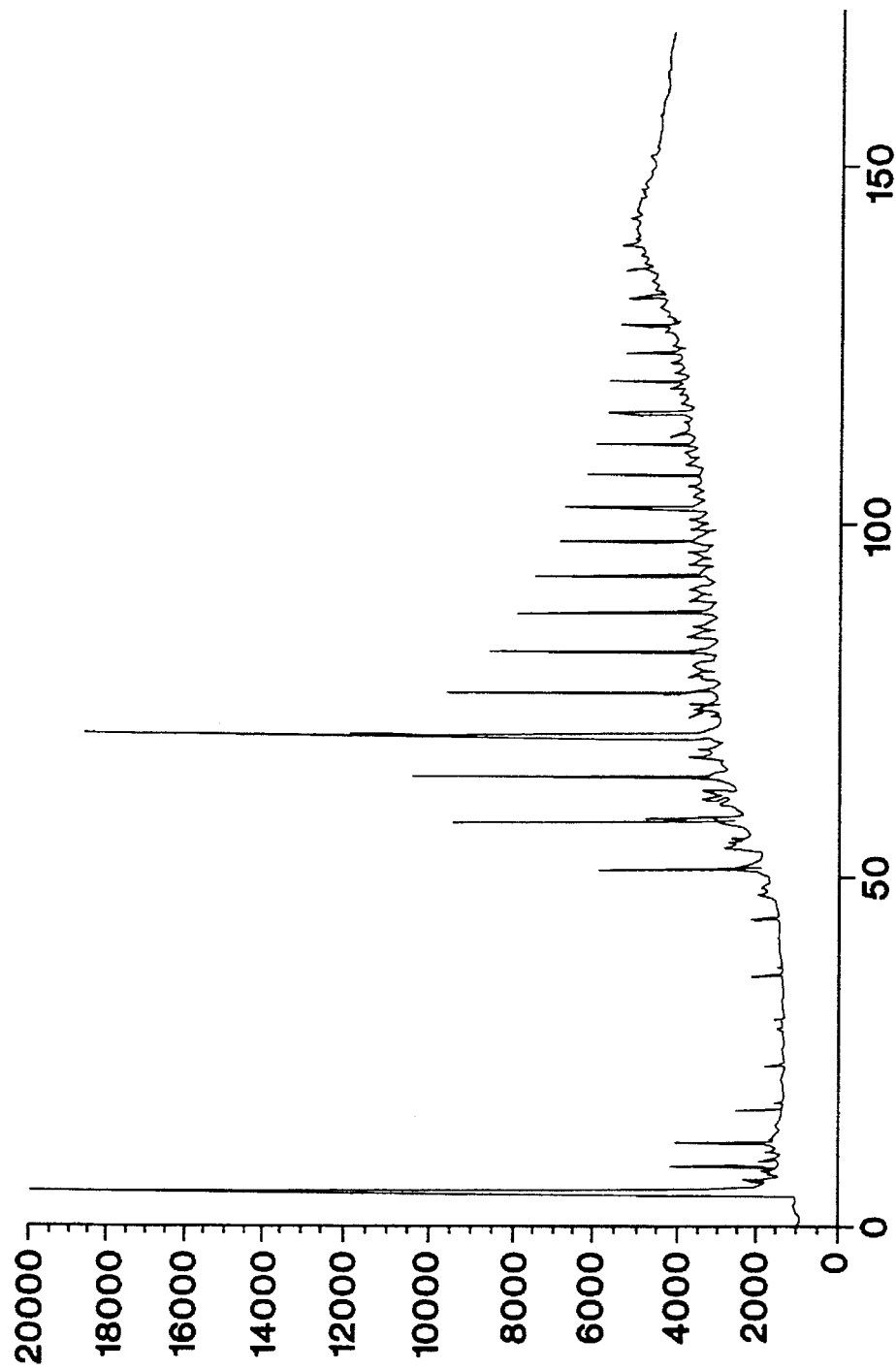
Figure 18:
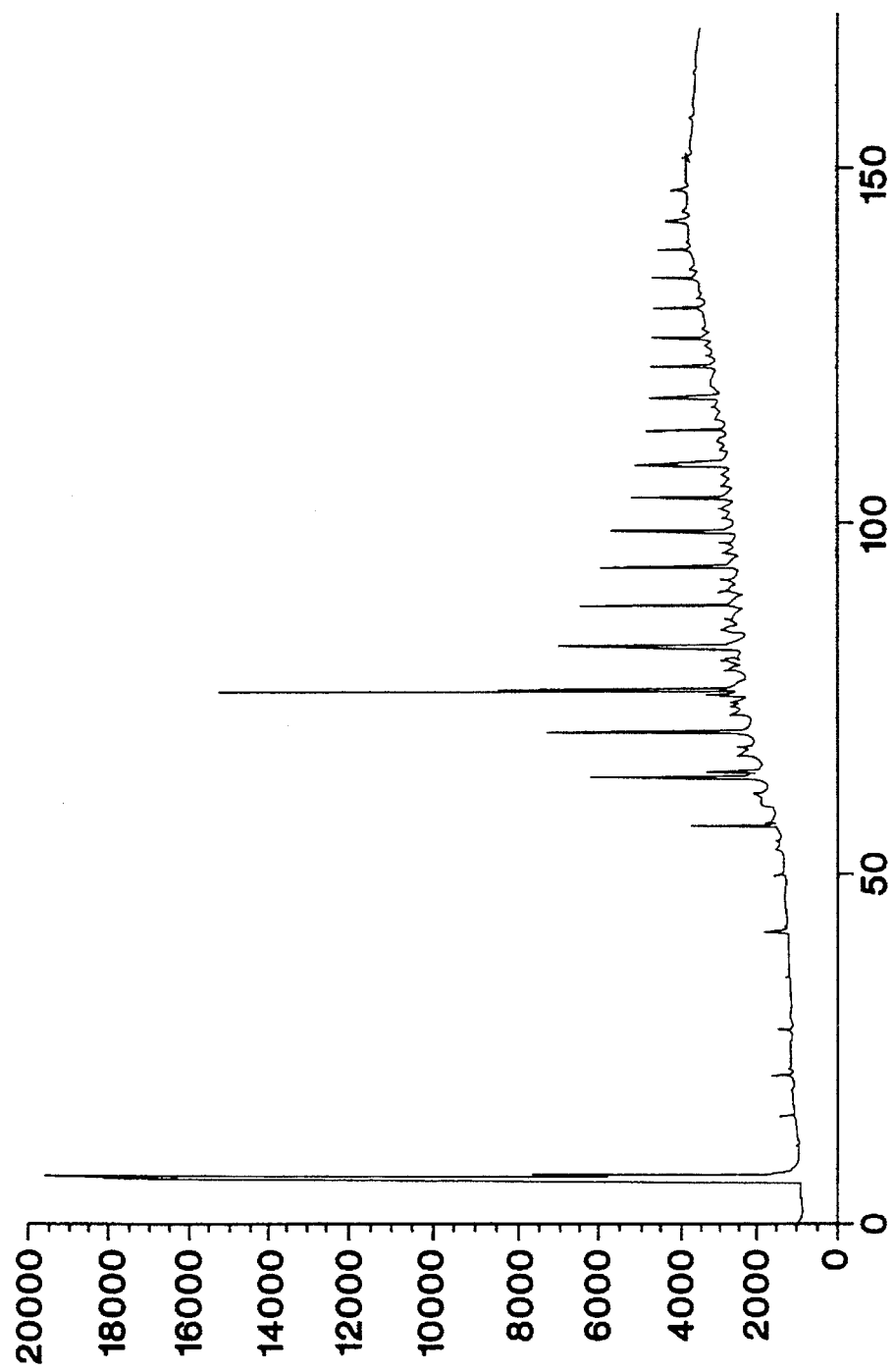

The results obtained from hydrocarbon analyses are given in FIG. 14 and in the chromatograms of FIGS. 15 to 18.

An interpretation of the evolution of the various fractions of crude made it possible to estimate if biodegradation had occurred. Thus, where oil biodegradation had occurred, a reduction in the alkane and aromatic fraction was observed accompanied by an increase in asphaltene and resin fractions.

On FIG. 14, it can be seen that there was a decrease in alkane fraction in the 3 tanks after 42 days, but the increase in the asphaltene+ resin fraction is greater in the tank treated with acylated meal. This result, which demonstrates that biodegradation was greater in the tank treated with acylated meal is corroborated by the chromatograms given at the end of this document. It can in fact be observed that there is a distinct dropoff in the alkane fraction between 0 and 42 days and this reduction is greater for the tank that was treated with the acylated meal.

The complete set of results obtained after 42 days shows that the presence of the acylated meal favors hydrocarbon biodegradation. The results are even more significant after a longer period, 42 days being a period of time considered fairly short for observing hydrocarbon biodegradation.

Moreover, visual observation made it possible to state that the acylated meal did not lead to the hydrocarbons flowing to the bottom of the tank.

This trial makes it possible to highlight the value of treating a hydrocarbon slick or layer with acylated animal meal. The value of this is even more significant in view of the fact that there are no or only few biodegradation additives available for treating floating oil slicks.

What is claimed is:

1. A biodegradation enhancing additive consisting of a mixture comprising:
   (i) at least one source of assimilable nitrogen consisting of at least one unsubstituted or substituted aminated acid selected from the group consisting of lysine, methionine, cystine, threonine, tryptophan, hydroxylysine, hydroxyproline, and mixtures thereof;
   (ii) at least one source of phosphorous;
in a nitrogen/phosphorous (N/P) ratio of from 2 to 100; said additive having been subjected to a treatment designed to render said additive oleophilic.

2. The biodegradation-enhancing additive according to claim 1, wherein said treatment consists of an acylation reaction.

3. The biodegradation-enhancing additive according to claim 2, wherein said acylation is carried out using laurylic acid chloride.

4. The biodegradation-enhancing additive according to claim 1, wherein said source of assimilable nitrogen represents at least 5% by weight of the total weight of said additive.

5. The biodegradation-enhancing additive according to claim 14, wherein said source of assimilable nitrogen occurs in proteins representing at least 50% by weight of the total weight of said additive.

6. The biodegradation-enhancing additive according to claim 1, wherein said source of phosphorous is a mineral salt of phosphorous.

7. The biodegradation-enhancing additive according to claim 1, wherein said nitrogen/phosphorous ratio is comprised in the range of from 4 to 40..

8. The biodegradation-enhancing additive according to claim 7, wherein said nitrogen/phosphorous ratio is equal to about 16.

9. A biodegradation-enhancing additive for the biodegradation of hydrocarbons, said additive consisting of a mixture comprising:
   (i) at least one source of assimilable nitrogen consisting of at least one unsubstituted or substituted aminated acid;
   (ii) at least one source of phosphorous;
in a nitrogen/phosphorous (N/P) ratio of from 2 to 100; said additive having been subjected to a treatment designed to render said additive oleophilic, and wherein said additive is an animal meal.

10. The biodegradation-enhancing additive according to claim 9, wherein said animal meal consists of a fish meal.

11. The biodegradation-enhancing additive according to claim 9, wherein said animal meal is of meat origin.

12. The biodegradation-enhancing additive according to claim 9, wherein said treatment consists of an acylation reaction.

13. The biodegradation-enhancing additive according to claim 9, wherein said acylation is carried out using laurylic acid chloride.

14. The biodegradation-enhancing additive according to claim 9, wherein said source of assimilable nitrogen represents at least by weight of the total weight of said additive.

15. The biodegradation-enhancing additive according to claim 1, wherein said source of assimilable nitrogen occurs in proteins representing at least 50% by weight of the total weight of said additive.

16. The biodegradation-enhancing additive according to claim 9, wherein said source of phosphorous is a mineral salt of phosphorous.

17. The biodegradation-enhancing additive according to claim 9, wherein said nitrogen/phosphorous ratio is comprised in the range of from 4 to 40.

18. The biodegradation-enhancing additive according to claim 9, wherein said nitrogen/phosphorous ratio is equal to about 16.

19. A process for the biodegradation of hydrocarbons comprising the step of applying a biodegradation-enhancing additive according to claims 1 or 9 to the surface of a hydrocarbon-polluted medium.

20. The process according to claim 19, wherein said additive is present in a weight ratio of additive to hydrocarbon comprised between 3 and 30.

21. The process according to claim 20, wherein said additive is present in a weight ratio of additive to hydrocarbon equal to about 10.

* * * * *